US012629817B2

(12) United States Patent　　　　　(10) Patent No.:　US 12,629,817 B2
　　Kwon et al.　　　　　　　　　　　　　(45) Date of Patent:　　May 19, 2026

(54) SURGICAL DOUBLE PARALLELOGRAM DEVICE

(71) Applicants: ROEN SURGICAL INC., Daejeon (KR); KOREA ADVANCED INSTITUTE OF SCIENCE AND TECHNOLOGY, Daejeon (KR)

(72) Inventors: Dong-Soo Kwon, Daejeon (KR); Un-Je Yang, Daejeon (KR); Chang-Kyun Kim, Daejeon (KR); Duk-Sang Kim, Daejeon (KR)

(73) Assignees: ROEN SURGICAL INC., Yuseong-gu (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 157 days.

(21) Appl. No.: 18/036,868

(22) PCT Filed: Nov. 11, 2021

(86) PCT No.: PCT/KR2021/016397
§ 371 (c)(1),
(2) Date: May 12, 2023

(87) PCT Pub. No.: WO2022/103166
PCT Pub. Date: May 19, 2022

(65) Prior Publication Data
US 2023/0415332 A1　　Dec. 28, 2023

(30) Foreign Application Priority Data
Nov. 13, 2020　(KR) ........................ 10-2020-0151617

(51) Int. Cl.
　　*B25J 9/10*　　　　(2006.01)
　　*A61B 90/50*　　　(2016.01)
　　*B25J 9/08*　　　　(2006.01)

(52) U.S. Cl.
CPC ............. *B25J 9/1065* (2013.01); *A61B 90/50* (2016.02); *B25J 9/08* (2013.01); *A61B 2090/506* (2016.02)

(58) Field of Classification Search
CPC . B25J 9/1065; B25J 9/08; B25J 9/1689; B25J 3/02; A61B 90/50; A61B 2090/506;
(Continued)

(56) References Cited

U.S. PATENT DOCUMENTS 4,003,536 A * 1/1977 Sekerich ............ F16M 11/2092
　　　　　　　　　　　　　　　　　　　　　　　248/585
4,927,127 A * 5/1990 Lock ...................... A61G 13/02
　　　　　　　　　　　　　　　　　　　　　　　254/122
(Continued)

FOREIGN PATENT DOCUMENTS

CN　　105710864 A　　6/2016
CN　　107157581 A　　9/2017
(Continued)

OTHER PUBLICATIONS

International search report of PCT/KR2021/016397, Mar. 2, 2022, English translation.
(Continued)

*Primary Examiner* — Victor L MacArthur
(74) *Attorney, Agent, or Firm* — STIP Law Group, LLC

(57) ABSTRACT

The present invention relates to a surgical double parallelogram device, and to a surgical double parallelogram device in which respective pitch and roll module units form a double parallelogram while pitch- and roll-rotating. To this end, disclosed is the surgical double parallelogram device comprising: a plurality of pitch and roll module units in which each module forms a plurality of stages and which provides two degrees of freedom for each module to be capable of dependently pitch- and roll-rotating; and a plu-
(Continued)

rality of pitch link units connected to the plurality of pitch and roll module units to form a double parallelogram.

5 Claims, 11 Drawing Sheets

(58) Field of Classification Search
CPC ........... A61B 34/30; A61B 2017/00398; A61F 9/007; A61F 9/00727; G05B 2219/39389; G05B 2219/40415
See application file for complete search history.

(56) References Cited

U.S. PATENT DOCUMENTS

| | | | | |
|---|---|---|---|---|
| 6,702,805 | B1 * | 3/2004 | Stuart .................... | A61B 34/71 |
| | | | | 606/1 |
| 10,322,514 | B2 * | 6/2019 | Vander Poorten ..... | B25J 18/007 |
| 2015/0297934 | A1 * | 10/2015 | Agrawal .............. | A61H 1/0266 |
| | | | | 482/4 |
| 2016/0100900 | A1 | 4/2016 | Madhani et al. | |
| 2024/0058583 | A1 * | 2/2024 | Boulangé .......... | A61M 25/0113 |

FOREIGN PATENT DOCUMENTS

| | | | |
|---|---|---|---|
| JP | 2005198700 | A | 7/2005 |
| KR | 20090119366 | A | 11/2009 |
| KR | 101787265 | B1 | 10/2017 |
| KR | 20180097423 | A | 8/2018 |
| KR | 20200124056 | A | 11/2020 |
| WO | WO2013029069 | A1 | 3/2013 |

OTHER PUBLICATIONS

The extended European search report of EP21 89 2333, Oct. 23, 2024.
Office Action issued by the China National Intellectual Property Administration (CNIPA) concerning CN patent application No. 202180076317.1, Jan. 23, 2026, English Translation.

* cited by examiner

SURGICAL DOUBLE PARALLELOGRAM DEVICE

CROSS-REFERENCE TO RELATED APPLICATIONS

This application is the U.S. National Phase under 35 U.S.C. § 371 of International Application No. PCT/KR2021/016397, filed on Nov. 11, 2021, which in turn claims the benefit of Korean Application No. 10-2020-0151617, filed on Nov. 13, 2020, the disclosures of which are incorporated by reference into the present application.

TECHNICAL FIELD

The present invention relates to a surgical double parallelogram device, and more particularly, to a surgical double parallelogram device in which respective pitch and roll module units form a double parallelogram while pitch- and roll-rotating.

BACKGROUND ART

In general, a parallelogram may have only one degree of freedom. In order to secure two degrees of freedom, single-axis rotation is realized so that pitch rotation is realized by the parallelogram, and roll rotation is performed by driving a motor. A typical two degrees of freedom realization device using the parallelogram and the motor has a problem of insufficient precision and rigidity of the corresponding degree of freedom.

DISCLOSURE OF THE INVENTION

Technical Problem

In order to solve the above-described problem, the present invention provides a device performing a two degrees of freedom and RCM operation through a combination of each prismatic degree of freedom, which is advantageous for high precision, and minimizing backlash and friction.

The objects of the present invention are not limited to the aforementioned object, but other objects not described herein will be clearly understood by those skilled in the art from descriptions below.

Technical Solution

An embodiment of the present invention provides a surgical double parallelogram device characterized by including: a plurality of pitch and roll module units in which each module forms a plurality of stages and which provide two degrees of freedom for each module to dependently pitch-rotate and roll-rotate; and a plurality of pitch link units connected to the plurality of pitch and roll module units to form a double parallelogram.

Also, the plurality of pitch and roll module units may be jointly connected to each other by the plurality of pitch link units while being spaced a predetermined distance in parallel from each other in a first direction.

Also, the plurality of pitch link units may jointly connect the plurality of pitch and roll module units in a second direction perpendicular to the first direction.

Also, each of the plurality of pitch and roll module units may include: a base link unit jointly connected to the plurality of pitch link units in the second direction; a roll link unit connected to the base link unit to roll-rotate; a pitch joint unit configured to jointly connect the base link unit and the plurality of pitch link units so that each of the base link unit and the plurality of pitch line units pitch-rotates; and a roll joint unit configured to jointly connect the base link unit and the roll link unit so that each of the base link unit and the roll link unit roll-rotates.

Also, the first and fourth base link units may be jointly connected to the plurality of pitch link units at two points on each of the left and right sides, and the second and third base link units may be jointly connected to the plurality of pitch link units at three points on each of the left and right sides.

Also, the first and fourth base link units may be disposed at outermost portions, respectively, and the second and third base link units may be disposed in spaces between the first and fourth base link units, respectively.

Also, the plurality of pitch link units may include: first, second, and third left pitch link units spaced a predetermined distance in parallel from each other so as to be jointly connected to the plurality of base link units in the second direction and at the left side; and first, second, and third right pitch link units spaced a predetermined distance in parallel from each other so as to be jointly connected in pairs to the plurality of base link units in the second direction and at the right side.

Also, the plurality of pitch and roll module units may include: a first pitch and roll module unit in which each of the first and second left pitch link units and the first and second right pitch link units is jointly connected in pairs to the first base link unit; a second pitch and roll module unit in which each of the first, second, and third left pitch link units and the first, second, and third right pitch link units is jointly connected in pairs to the second base link unit; a third pitch and roll module unit in which each of the first, second, and third left pitch link units and the first, second, and third right pitch link units is jointly connected in pairs to the third base link unit; and a fourth pitch and roll module unit in which each of the second and third left pitch link units and the second and third right pitch link units is jointly connected in pairs to the fourth base link unit.

Also, a surgical end-effector may be connected and coupled to one roll link unit of the first and second pitch and roll module units, and a driving unit may be connected and coupled to the other roll link unit of the third and fourth pitch and roll module units.

In another embodiment of the present invention, a surgical double parallelogram device is characterized by including: a first parallelogram module unit configured to form a first parallelogram at one side based on a virtual vertical axis; and a second parallelogram module unit configured to form a second parallelogram so as to contact in parallel to the first parallelogram.

Also, the first parallelogram at a side adjacent to the connected surgical end-effector may be formed at a relatively higher position than the second parallelogram while partially overlapping to perform intraocular surgery.

Also, the first parallelogram at a side adjacent to the connected surgical end-effector may be formed at a relatively lower position than the second parallelogram while partially overlapping to perform suture surgery.

Also, each of the first and second parallelograms may be formed according to a connection combination of respective joint connection points of first, second, third, and fourth base link units arranged to form a plurality of stages spaced a predetermined distance in parallel from each other in a first direction and the first, second, and third pitch link units jointly connected at one side of the first, second, third, and fourth base link units in a second direction perpendicular to the first direction.

Also, the first and fourth base link units may be disposed at outermost portions, respectively, and the second and third base link units may be disposed in spaces between the first and fourth base link units, respectively.

Also, the first parallelogram module unit may include: first, second, and third base link units connected through first joint connection at each of at least two points of one side thereof; and first and second pitch link units jointly connected at one side of the first, second, and third base link units in the second direction perpendicular to the first direction, and the first joint connection points may be connected to form a first parallelogram.

Also, the second parallelogram module unit may include: second, third, and fourth base link units connected through second joint connection at each of at least two points of one side thereof; and second and third pitch link units jointly connected at one side of the second, third, and fourth base link units in the second direction perpendicular to the first direction, and the second joint connection points may be connected to form a second parallelogram.

In still another embodiment of the present invention, a surgical double parallelogram device is characterized by including: a first parallelogram module unit configured to form a first parallelogram at one side based on a virtual vertical axis; and a second parallelogram module unit configured to form a second parallelogram so as to contact in parallel to the first parallelogram, thereby performing pituitary surgery.

Also, the first parallelogram at a side adjacent to the connected surgical end-effector may be formed at a relatively lower position than the second parallelogram while partially overlapping to perform the pituitary surgery.

Also, each of the first and second parallelograms may be formed according to a connection combination of respective joint connection points of first, second, and third, and fourth base link units arranged to form a plurality of stages spaced a predetermined distance in parallel from each other in a first direction and the first, second, and third pitch link units jointly connected at one side of the first, second, third, and fourth base link units in a second direction perpendicular to the first direction, thereby performing the pituitary surgery.

Also, the first and fourth base link units may be disposed at outermost portions, respectively, and the second and third base link units may be disposed in spaces between the first and fourth base link units, respectively, thereby performing the pituitary surgery.

Also, the first parallelogram module unit may include: first, second, and third base link units connected through first joint connection at each of at least two points of one side thereof; and first and second pitch link units jointly connected at one side of the first, second, and third base link units in a second direction perpendicular to the first direction, and the first joint connection points may be connected to form a first parallelogram, thereby performing the pituitary surgery.

Also, the second parallelogram module unit may include: second, third, and fourth base link units connected through second joint connection at each of at least two points of one side thereof; and second and third pitch link units jointly connected at one side of the second, third, and fourth base link units in a second direction perpendicular to the first direction, and the second joint connection points may be connected to form a second parallelogram, thereby performing the pituitary surgery.

Advantageous Effects

According to the above-described present invention, the effects of performing the two degrees of freedom and RCM operation through the combination of each prismatic degree of freedom, which is advantageous for the high precision, and minimizing the backlash and friction are obtained.

BRIEF DESCRIPTION OF THE DRAWINGS

The following drawings attached in this specification illustrate a preferred embodiment of the present invention and function to make further understood the technical spirit of the present invention along with the detailed description of the invention, and thus, the present invention should not be construed as being limited to only the drawings. In the drawings:

FIG. 13 is a view illustrating a double parallelogram device for pituitary surgery according to a third embodiment of the present invention;

FIG. 15 is a view illustrating a state in which a driving unit and a surgical end-effector are coupled to the double parallelogram device for pituitary surgery according to the third embodiment of the present invention.

MODE FOR CARRYING OUT THE INVENTION

Hereinafter, a preferred embodiment of the present invention will be described with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the inventive concept to those skilled in the art. Moreover, detailed descriptions related to well-known functions or configurations will be ruled out in order not to unnecessarily obscure subject matters of the present invention. It will be apparent to those skilled in the art that various modifications and variations can be made in the present invention without departing form the spirit or scope of the invention.

First Embodiment: Double Parallelogram Device for Intraocular Surgery

As illustrated in FIGS. 1 to 9, a double parallelogram device for intraocular surgery according to a first embodiment of the present invention forms a double parallelogram and pitch- and roll-rotates according to control driving of a driving unit 10 to determine an orientation and a position of a surgical end-effector 20. For example, the intraocular surgery includes retinal surgery. Hereinafter, the double parallelogram device for intraocular surgery according to a first embodiment of the present invention will be described in detail with reference to accompanying FIGS. 1 to 9.

Figure 1:
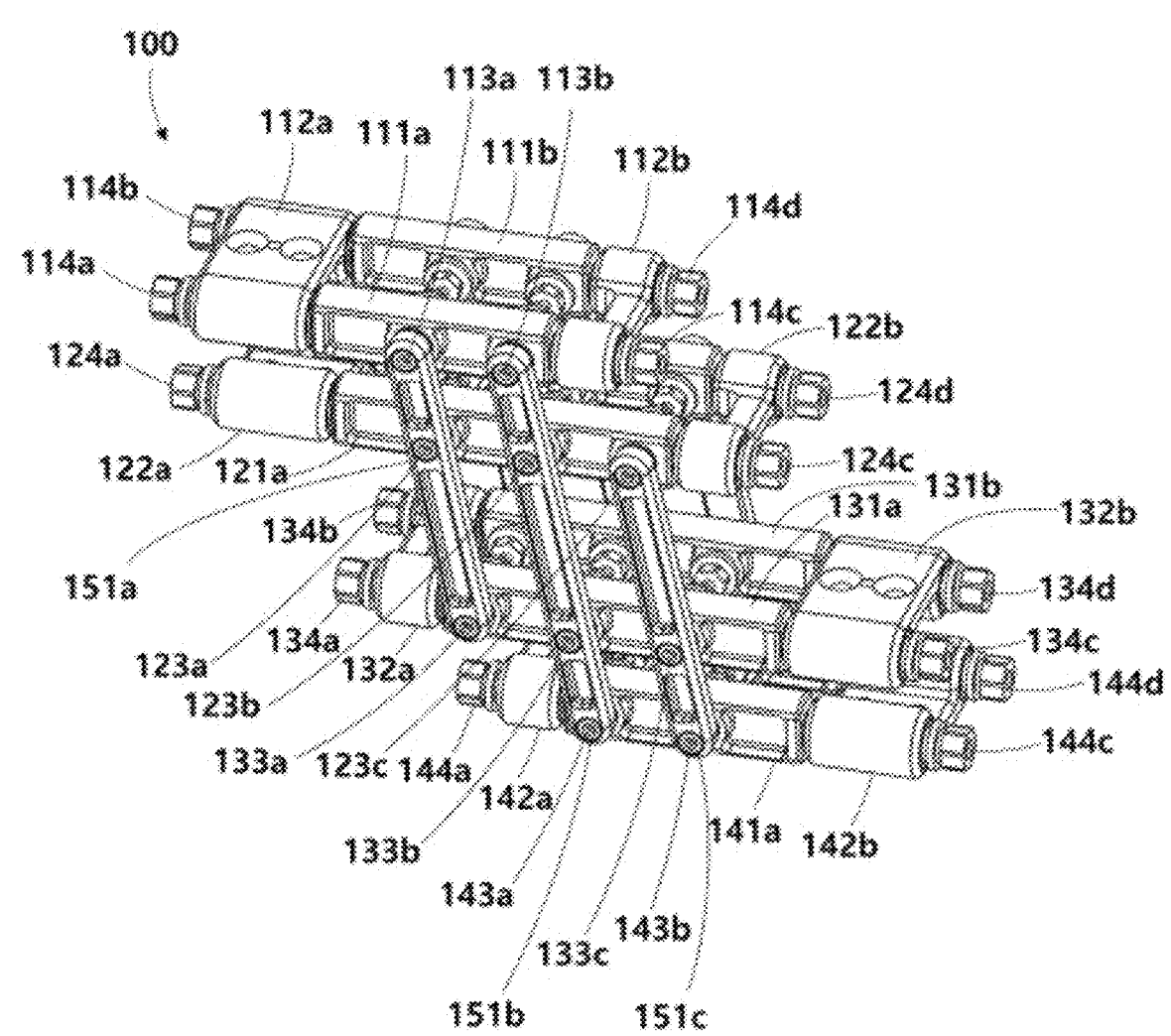
FIGS. 1 and 2 are views illustrating a double parallelogram device for intraocular surgery according to a first embodiment of the present invention.
Figure 2:
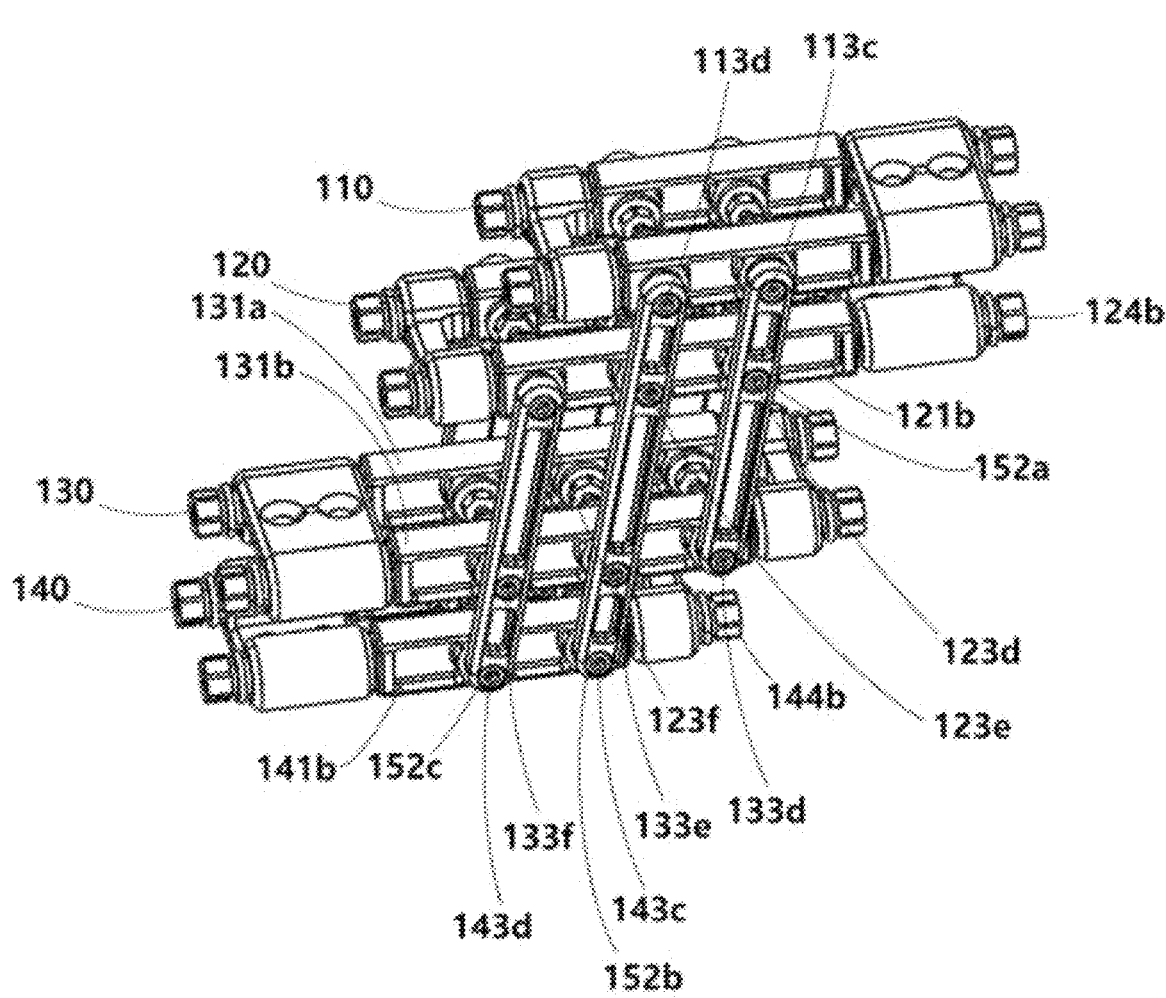

Referring to FIGS. 1 and 2, a double parallelogram unit 100 for ocular surgery includes first, second, third, and fourth pitch and roll module units 110, 120, 130, and 140.

A first pitch and roll module unit 110 include a first base link unit, a first roll link unit, a first pitch joint unit, and a first roll joint unit.

The first base link unit includes a left base link unit 111a and a right base link unit 111b based on FIGS. 1 and 2. The terms left and right may be replaced with other terms depending on a posture position of the dual parallelogram unit 100 for ocular surgery. Although the left base link unit 111a and the right base link unit 111b are separated from each other, the left base link unit 111a and the right base link unit 111b may be integrated with each other as necessary.

The left base link unit 111a and first and second left pitch link units 151a and 151b are jointly connected to each other at two points to pitch-rotate by first and second left pitch joint units 113a and 113b. The first and second left pitch link units 151a and 151b are jointly connected to the left base link unit 111a while being spaced a predetermined distance from each other in a horizontal direction (first direction).

The right base link unit 111b and first and second right pitch link units 152a and 152b are jointly connected to each other to pitch-rotate by first and second right pitch joint units 113c and 113d. The first and second right pitch link units 152a and 152b are jointly connected to the right base link unit 111b while being spaced a predetermined distance from each other in the horizontal direction. Thus, the right base link unit 111b and first and second right pitch link units 152a and 152b are jointly connected at total four points of left and right sides.

The joint connection between the left base link unit 111a and the first and second left pitch link units 151a and 151b and the joint connection between the right base link unit 111b and the first and second right pitch link units 152a and 152b are connected to each other in symmetrical pairs.

The left and right base link units 111a and 111b and a front roll link unit 112a disposed in the front are jointly connected to each other to roll-rotate by left and right front roll joint units 114a and 114b. Also, the left and right base link units 111a and 111b and a rear roll link unit 112b disposed in the rear are jointly connected to each other to roll-rotate by left and right rear roll joint units 114c and 114d.

The above-described first pitch and roll module unit 110 pitch-rotates based on the first and second left pitch joint units 113a and 113b and the first and second right pitch joint units 113c and 113d. Also, the first pitch and roll module unit 110 roll-rotates by the front and rear roll link units 112a and 112b and the left and right and front and rear roll joint units 114a, 114b, 114c and 114d.

A second pitch and roll module unit 120 includes a second base link unit, a second roll link unit, a second pitch joint unit, and a second roll joint unit.

The second base link unit includes a left base link unit 121a and a right base link unit 121b based on FIGS. 1 and 2. Although the left base link unit 121a and the right base link unit 121b are separated from each other, the left base link unit 121a and the right base link unit 121b may be integrated with each other as necessary.

The left base link unit 121a and first, second, and third left pitch link units 151a, 151b, and 151c are jointly connected to each other at three points to pitch-rotate by first, second, and third left pitch joint units 123a, 123b, and 123c. The first, second, and third left pitch link units 151a, 151b, and 151c are jointly connected to the left base link unit 121a at three points while being spaced a predetermined distance from each other in the horizontal direction.

The right base link unit 121b and first, second, and third right pitch link units 152a, 152b, and 152c are jointly connected to each other at three points to pitch-rotate by first, second, and third right pitch joint units 123d, 123e, and 123f. The first, second, and third right pitch link units 152a, 152b, and 152c are jointly connected at three points with the right base link unit 121b while being spaced a predetermined distance from each other in the horizontal direction. Thus, the first, second, and third right pitch link units 152a, 152b, and 152c and the right base link unit 121b are jointly connected at total six points of the left and right sides.

The joint connection between the left base link unit 121a and the first, second, and third left pitch link units 151a, 151b, and 151c and the joint connection between the right base link unit 121b and the first, second, and third right pitch link units 152a, 152b, and 152c are connected to each other in symmetrical pairs.

The left and right base link units 121a and 121b and a front roll link unit 122a disposed in the front are jointly connected to each other to roll-rotate by left and right front roll joint units 124a and 124b. Also, the left and right base link units 121a and 121b and a rear roll link unit 122b disposed in the rear are jointly connected to each other to roll-rotate by left and right rear roll joint units 124c and 124d.

The above-described second pitch and roll module unit 120 pitch-rotates based on the first, second, and third left pitch joint units 123a, 123b, and 123c and the first, second, and third right pitch joint units 123d, 123e, and 123f. Also, the second pitch and roll module unit 120 roll-rotates by the front and rear roll link units 122a and 122b and the left and right and front and rear roll joint units 124a, 124b, 124c and 124d.

A third pitch and roll module unit 130 includes a third base link unit, a third roll link unit, a third pitch joint unit, and a third roll joint unit.

The third base link unit includes a left base link unit 131a and a right base link unit 131b based on FIGS. 1 and 2. Although the left base link unit 131a and the right base link unit 131b are separated from each other, the left base link unit 131a and the right base link unit 131b may be integrated with each other as necessary.

The left base link unit 131a and first, second, and third left pitch link units 151a, 151b, and 151c are jointly connected to each other at three points to pitch-rotate by first, second, and third left pitch joint units 133a, 133b, and 133c. The first, second, and third left pitch link units 151a, 151b, and 151c are jointly connected to the left base link unit 131a at three points while being spaced a predetermined distance from each other in the horizontal direction.

The right base link unit 131b and the first, second, and third right pitch link units 152a, 152b, and 152c are jointly connected to each other at three points to pitch-rotate by first, second, and third right pitch joint units 133d, 133e, and 133f. The first, second, and third right pitch link units 152a, 152b, and 152c are jointly connected at three points with the right base link unit 131b while being spaced a predetermined distance from each other in the horizontal direction. Thus, the first, second, and third right pitch link units 152a, 152b, and 152c and the right base link unit 121b are jointly connected at total six points of the left and right sides.

The joint connection between the left base link unit 131a and the first, second, and third left pitch link units 151a, 151b, and 151c and the joint connection between the right base link unit 131b and the first, second, and third right pitch link units 152a, 152b, and 152c are connected to each other in symmetrical pairs.

The left and right base link units 131a and 131b and a front roll link unit 132a disposed in the front are jointly connected to each other to roll-rotate by left and right front roll joint units 134a and 134b. Also, the left and right base link units 131a and 131b and a rear roll link unit 132b disposed in the rear are jointly connected to each other to roll-rotate by left and right rear roll joint units 134c and 134d.

The above-described third pitch and roll module unit 130 pitch-rotates based on the first, second, and third left pitch joint units 133a, 133b, and 133c and the first, second, and third right pitch joint units 133d, 133e, and 133f. Also, the third pitch and roll module unit 130 roll-rotates by the front and rear roll link units 132a and 132b and the left and right and front and rear roll joint units 134a, 134b, 134c and 134d.

A fourth pitch and roll module unit 140 includes a fourth base link unit, a fourth roll link unit, a fourth pitch joint unit, and a fourth roll joint unit.

The fourth base link unit includes a left base link unit 141a and a right base link unit 141b based on FIGS. 1 and 2. Although the left base link unit 141a and the right base link unit 141b are separated from each other, the left base link unit 141a and the right base link unit 141b may be integrated with each other as necessary.

The left base link unit 141a and the first and second left pitch link units 151a and 151b are jointly connected to each other at two points to pitch-rotate by first and second left pitch joint units 143a and 143b. The first and second left pitch link units 151a and 152b are jointly connected to the left base link unit 141b while being spaced a predetermined distance from each other in the horizontal direction.

The right base link unit 141b and the first and second right pitch link units 152a and 152b are jointly connected to each other to pitch-rotate by first and second right pitch joint units 143c and 143d. The first and second right pitch link units 152a and 152b are jointly connected to the right base link unit 141b while being spaced a predetermined distance from each other in the horizontal direction. Thus, the right base link unit 141b and the first and second right pitch link units 152a and 152b are jointly connected at total four points of left and right sides.

The joint connection between the left base link unit 141a and the first and second left pitch link units 151a and 151b and the joint connection between the right base link unit 141b and the first and second right pitch link units 152a and 152b are connected to each other in symmetrical pairs.

The left and right base link units 141a and 141b and a front roll link unit 142a disposed in the front are jointly connected to each other to roll-rotate by left and right front roll joint units 144a and 144b. Also, the left and right base link units 141a and 141b and a rear roll link unit 142b disposed in the rear are jointly connected to each other to roll-rotate by left and right rear roll joint units 144c and 144d.

The above-described fourth pitch and roll module unit 140 pitch-rotates based on the first and second left pitch joint units 143a and 143b and the first and second right pitch joint units 143c and 143d. Also, the fourth pitch and roll module unit 140 roll-rotates by the front and rear roll link units 142a and 142b and the left and right and front and rear roll joint units 144a, 144b, 144c and 144d.

The first pitch and roll module unit 110 is disposed at an uppermost side based on FIGS. 1 and 2, and the second, third, and fourth pitch and roll module units 120, 130, and 140 are sequentially arranged in stages. The first, second, and third left pitch link units 151a, 151b, and 151c jointly connect left sides of the first, second, third, and fourth pitch and roll module units 110, 120, 130, and 140 in the vertical direction. The first, second, and third right pitch link units 152a, 152b, and 152c jointly connect right sides of the first, second, third, and fourth pitch and roll module units 110, 120, 130, and 140 in the vertical direction.

The first, second, and third left pitch link units 151a, 151b, and 151c and the first, second, and third right pitch link units 152a, 152b, and 152c are jointly connected with the first, second, third, and fourth pitch and roll module units 110, 120, 130, and 140 in symmetrical pairs.

Three virtual vertical lines that are spaced a predetermined distance in parallel from each other are formed by connecting respective joint connection points of the first and second left pitch joint units 113a and 113b, the first, second, and third left pitch joint units 123a, 123b, and 123c, and the first, second, and third left pitch joint units 133a, 133b, and 133c, and the first and second left pitch joints 143a and 143b in the vertical direction (second direction) based on FIGS. 1 and 2. Also, three virtual vertical lines that are spaced a predetermined distance in parallel from each other are formed at the right side according to the same principle.

When the joint connection points of the first and second left pitch joint units 113a and 113b, the first, second, and third left pitch joint units 123a, 123b, and 123c, and the first, second, and third left pitch joint units 133a, 133b, and 133c, and the first and second left pitch joints 143a and 143b are connected in the horizontal direction based on FIGS. 1 and 2, four virtual horizontal lines spaced a predetermined distance in parallel from each other are formed. Also, four virtual vertical lines spaced a predetermined distance in parallel from each other are formed at the right side according to the same principle.

The first and fourth pitch and roll module units 110 and 140 are jointly connected at two points in the horizontal direction. The two point joint connection of the first pitch and roll module unit 110 and the fourth pitch and roll module unit 140 are connected so that any one joint connection point is deviated while meeting each other on the virtual vertical line. Also, the second and third pitch and roll module units 120 and 130 are jointly connected at three points in the horizontal direction. When each joint connection point is connected in the horizontal and vertical directions, the double parallelogram in FIG. 8 may be formed, which will be described later.

Figure 3:
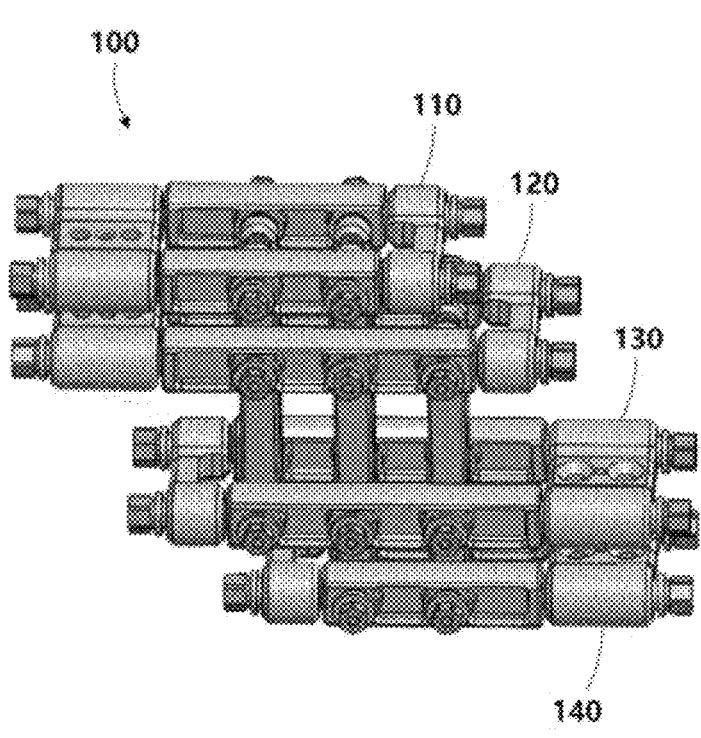
FIG. 3 is a view illustrating a state in which the double parallelogram device for intraocular surgery according to the first embodiment of the present invention is in a regular position instead of pitch-rotating.
Figure 4:
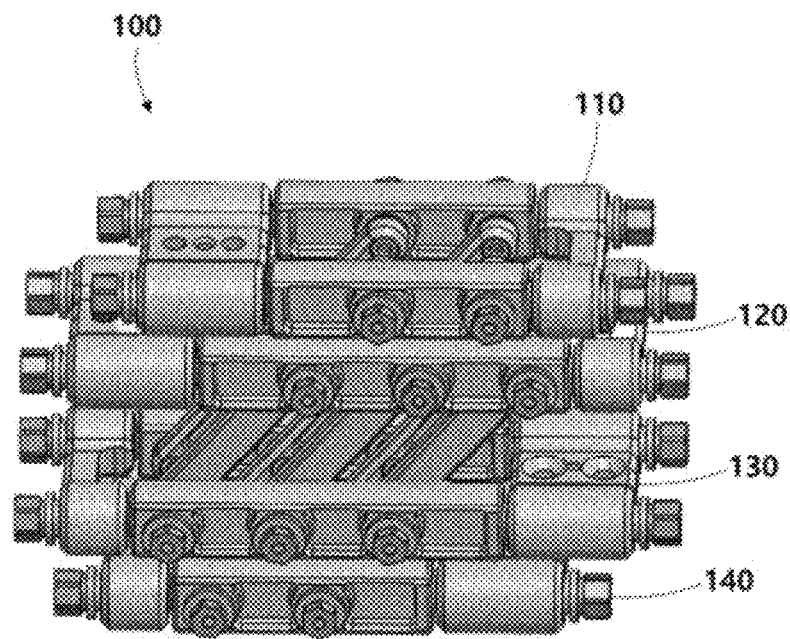
FIG. 4 is a view illustrating a state in which the double parallelogram device for intraocular surgery according to the first embodiment of the present invention pitch-rotates backward relatively to that of FIG. 3.
Figure 5:
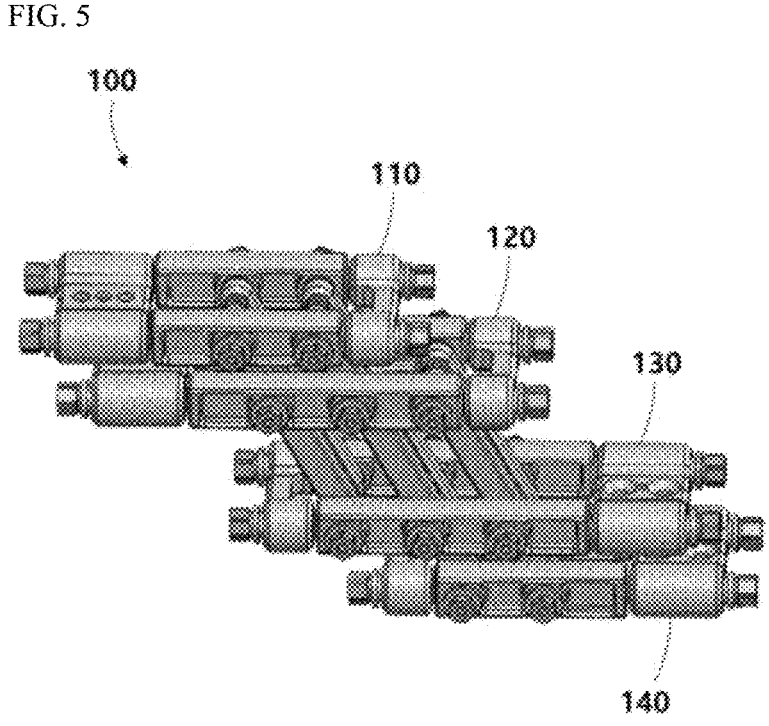
FIG. 5 is a view illustrating a state in which the double parallelogram device for intraocular surgery according to the first embodiment of the present invention pitch-rotates forward relatively to that of FIG. 3.

FIG. 3 is a view illustrating a state in which the double parallelogram unit 100 for ocular surgery does not pitch-rotate. Here, when a first pitch driving signal is transmitted by the driving unit 10, the double parallelogram unit 100 pitch-rotates backward based on one point as illustrated in FIG. 4, and when a second pitch driving signal is transmitted, the double parallelogram unit 100 pitch-rotates forward based on one point as illustrated in FIG. 5.

Figure 6:
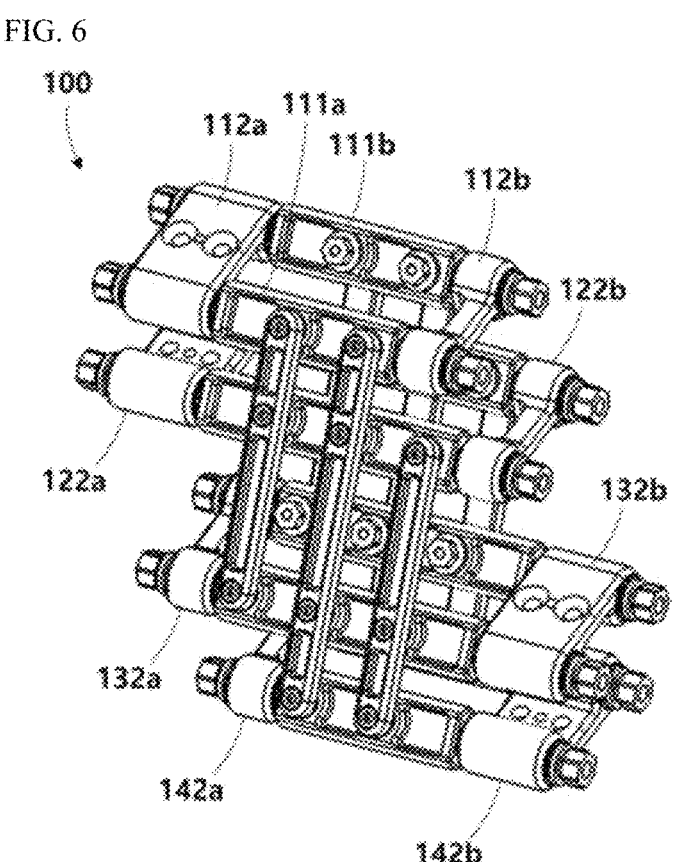
FIG. 6 is a view illustrating a state in which the double parallelogram device for intraocular surgery according to the first embodiment of the present invention roll-rotates in a first roll rotation direction.
Figures 7, 8:
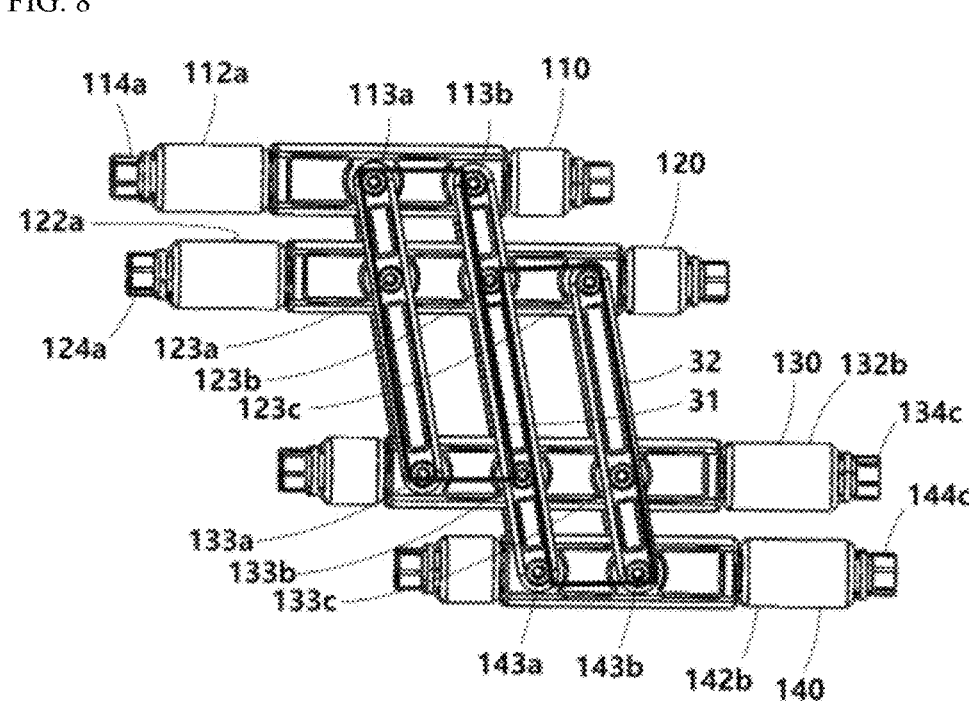
FIG. 7 is a view illustrating a state in which the double parallelogram device for intraocular surgery according to the first embodiment of the present invention roll-rotates in a second roll rotation direction.
FIG. 8 is a view illustrating first and second parallelograms of the double parallelogram device for intraocular surgery according to the first embodiment of the present invention.

FIG. 6 is a view illustrating a state in which the double parallelogram unit 100 for ocular surgery roll-rotates in a first roll rotation direction. When the double parallelogram unit 100 roll-rotates in the first roll rotation direction, the left base link units 111*a*, 121*a*, 131*a*, and 141*a* are disposed at a relatively lower position than the right base link units 111*b*, 121*b*, 131*b*, and 141*b*. FIG. 7 is a view illustrating a state in which the double parallelogram unit 100 for ocular surgery roll-rotates in a second roll rotation direction. When the double parallelogram unit 100 roll-rotates in the second roll rotation direction, the left base link units 111*a*, 121*a*, 131*a*, and 141*a* are disposed at a relatively higher position than the right base link units 111*b*, 121*b*, 131*b*, and 141*b*.

As illustrated in FIG. 8, a virtual first parallelogram 31 and a virtual second parallelogram 32 may be formed by connecting respective joint connection points of the first and second left pitch joint units 113*a* and 113*b*, the first, second, and third left pitch joint units 123*a*, 123*b*, and 123*c*, and the first, second, and third left pitch joint units 133*a*, 133*b*, and 133*c*, and the first and second left pitch joints 143*a* and 143*b* are connected in the horizontal and vertical directions based on FIG. 8. The first parallelogram 31 and the second parallelogram 32 are formed at left and right sides based on a virtual vertical line. The first parallelogram 31 is disposed higher than the second parallelogram 32

The first parallelogram 31 is formed by connecting respective joint connection points of the first and second left pitch joint units 113*a* and 113*b*, the first and second left pitch joint units 123*a* and 123*b*, and the first and second left pitch joint units 133*a* and 133*b* in a "rectangular shape" or a "square shape". The second parallelogram 32 is formed by connecting respective joint connection points of the second and third left pitch joint units 123*b* and 123*c*, the second and third left pitch joint units 133*b* and 133*c*, and the first and second left pitch joint units 143*a* and 143*b* in a "rectangular shape" or a "square shape". The first parallelogram 31 and the second parallelogram 32 share some overlapped joint units to contact each other.

Figure 9:
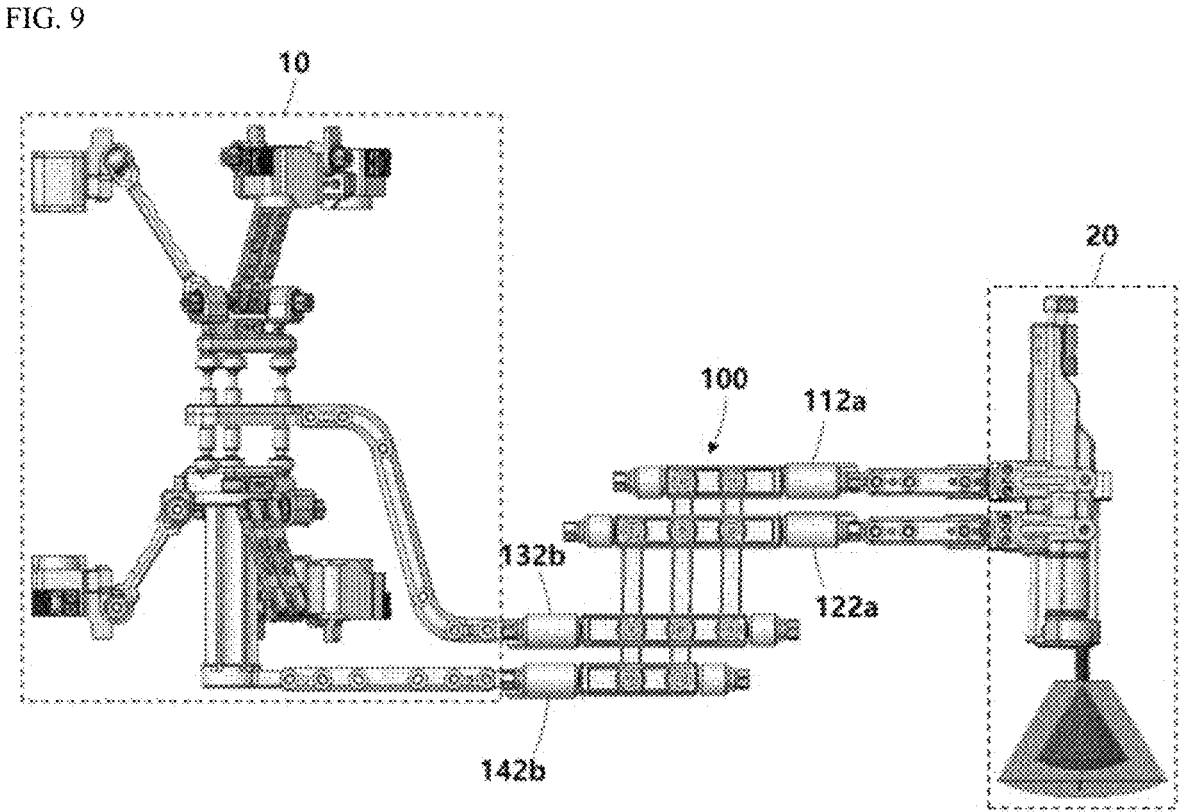
FIG. 9 is a view illustrating a state in which a driving unit and a surgical end-effector are coupled to the double parallelogram device for intraocular surgery according to the first embodiment of the present invention.

As illustrated in FIGS. 8 and 9, the surgical end-effector 20 is coupled to the first and second front roll link units 112*a* and 122*a* and the front roll joint units 114*a* and 124*a* disposed adjacent to the first parallelogram 31, and the driving unit 10 is coupled to the first and second rear roll link units 132*b* and 142*b* and the rear roll joint units 134*c* and 144*c* disposed adjacent to the second parallelogram 32.

Referring to FIGS. 4 to 7, the modules of respective stages are dependent on each other to pitch-rotate or roll-rotate according to a control driving signal. That is, the related modules of respective stages are dependent on each other to pitch-rotate during the pitch rotation, and the related modules of respective stages are dependent on each other to roll-rotate during the roll rotation.

Second Embodiment: Double Parallelogram for Suture Surgery

Figure 10:
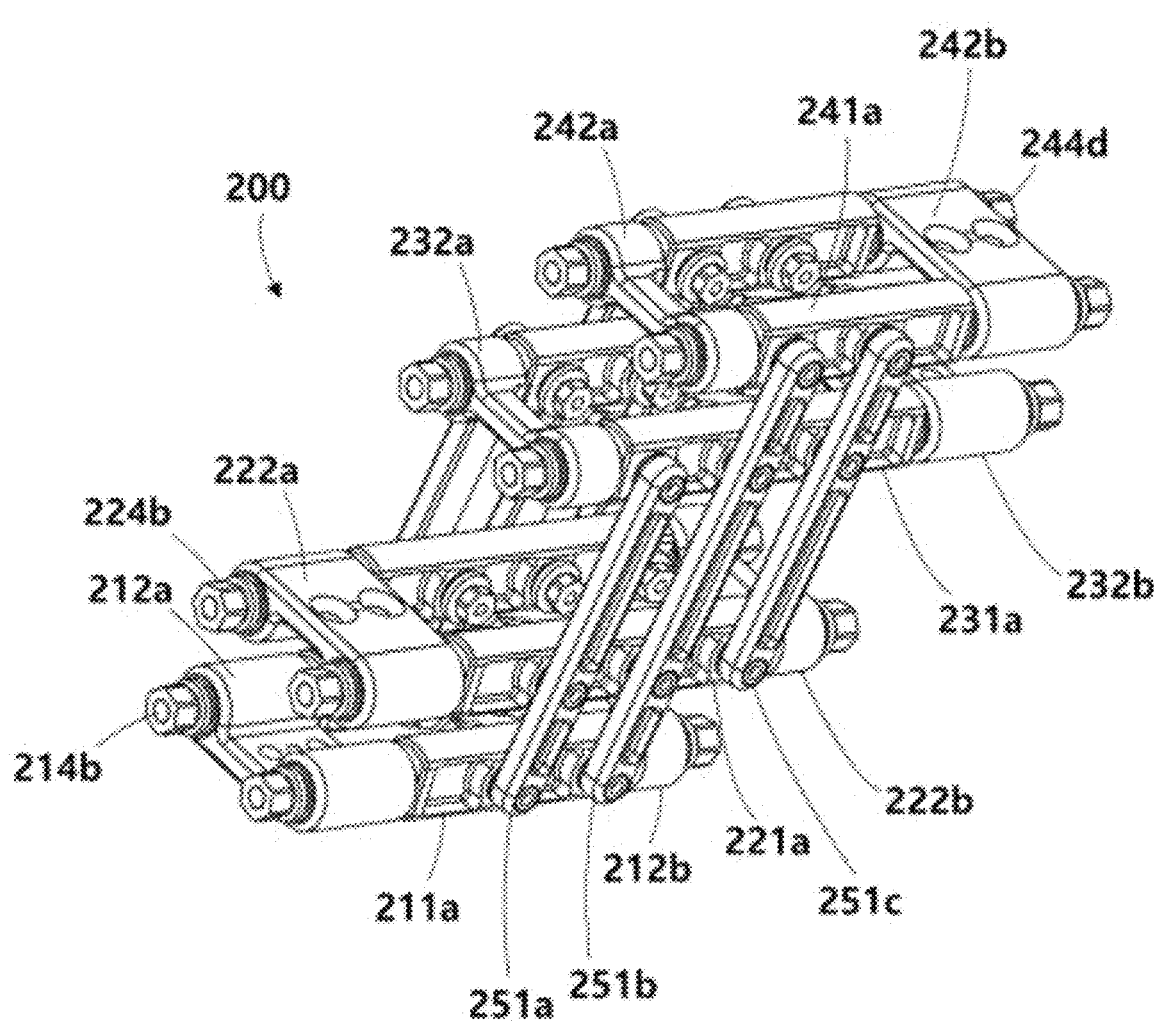
FIG. 10 is a view illustrating a double parallelogram device for suture surgery according to a second embodiment of the present invention.
Figure 11:
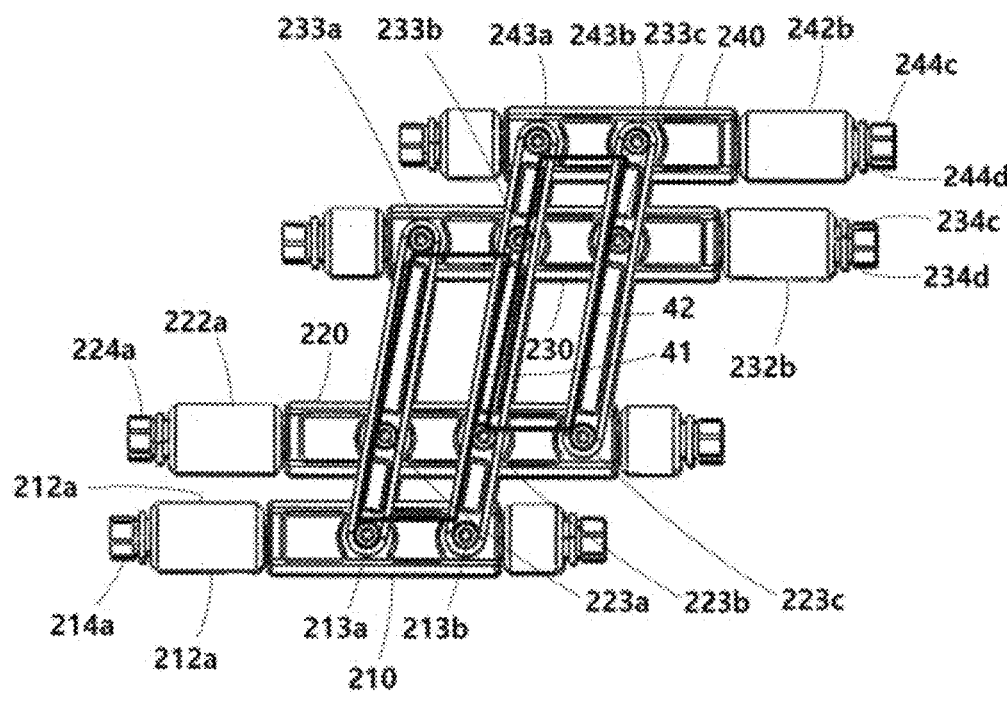
FIG. 11 is a view illustrating first and second parallelograms of the double parallelogram device for suture surgery according to the second embodiment of the present invention.
Figure 12:
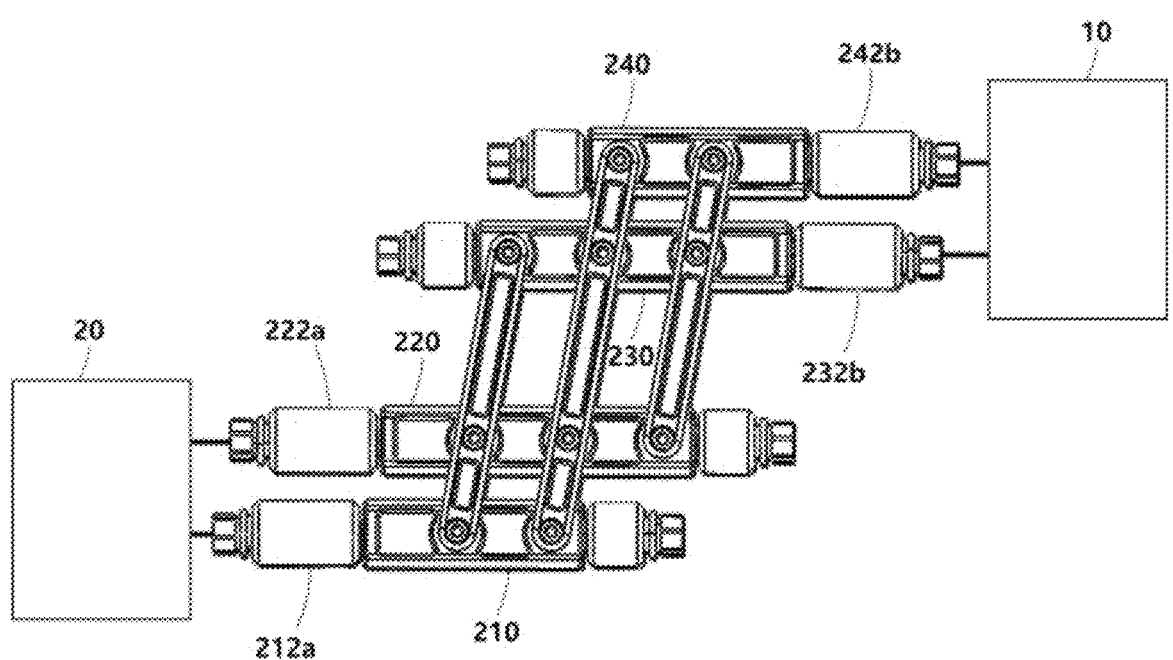
FIG. 12 is a view illustrating a state in which a driving unit and a surgical end-effector are coupled to the double parallelogram device for suture surgery according to the second embodiment of the present invention.

As illustrated in FIGS. 10 to 12, a double parallelogram device for suture surgery according to a second embodiment of the present invention forms a double parallelogram to pitch-rotate and roll-rotate according to a control driving of a driving unit 10, thereby allowing a surgical end-effector 20 to be oriented and positioned. The suture surgery includes, e.g., anastomosis of blood vessels and nerves. Hereinafter, the double parallelogram device for suture surgery according to the second embodiment of the present invention will be described in detail with reference to accompanying FIGS. 10 to 12.

Referring to FIGS. 1 and 10, a double parallelogram unit 200 for suture surgery may be obtained by rotating the double parallelogram unit 100 for intraocular surgery by 180°. Thus, descriptions of a configuration and a function of each unit will be replaced by those of the first embodiment.

As illustrated in FIG. 11, a virtual first parallelogram 41 and a virtual second parallelogram 42 may be formed by connecting respective joint connection points of first and second left pitch joint units 213*a* and 213*b*, first, second, and third left pitch joint units 223*a*, 223*b*, and 223*c*, first, second, and third left pitch joint units 233*a*, 233*b*, and 233*c*, and first and second left pitch joints 243*a* and 243*b* in the horizontal and vertical directions based on FIG. 11. The first parallelogram 41 and the second parallelogram 42 are formed at left and right sides based on a virtual vertical line. The first parallelogram 41 is disposed lower than the second parallelogram 42

The first parallelogram 41 is formed by connecting respective joint connection points of the first and second left pitch joint units 213*a* and 213*b*, the first and second left pitch joint units 223*a* and 223*b*, and the first and second left pitch joint units 233*a* and 233*b* in a "rectangular shape" or a "square shape". The second parallelogram 42 is formed by connecting respective joint connection points of second and third left pitch joint units 223*b* and 223*c*, second and third left pitch joint units 233*b* and 233*c*, and first and second left pitch joint units 243*a* and 243*b* in a "rectangular shape" or a "square shape". The first parallelogram 41 and the second parallelogram 42 share some overlapped joint units to contact each other.

As illustrated in FIGS. 11 and 12, a surgical end-effector 20 is coupled to first and second front roll link units 212*a* and 122*a* and front roll joint units 214*a*, 214*b*, 224*a*, and 224*b* disposed adjacent to the first parallelogram 41, and a driving unit 10 is coupled to first and second rear roll link units 232*b* and 242*b* and rear roll joint units 234*c*, 234*d*, 244*c*, and 244*d* disposed adjacent to the second parallelogram 42.

Third Embodiment: Double Parallelogram Device for Pituitary Surgery

Figure 13:
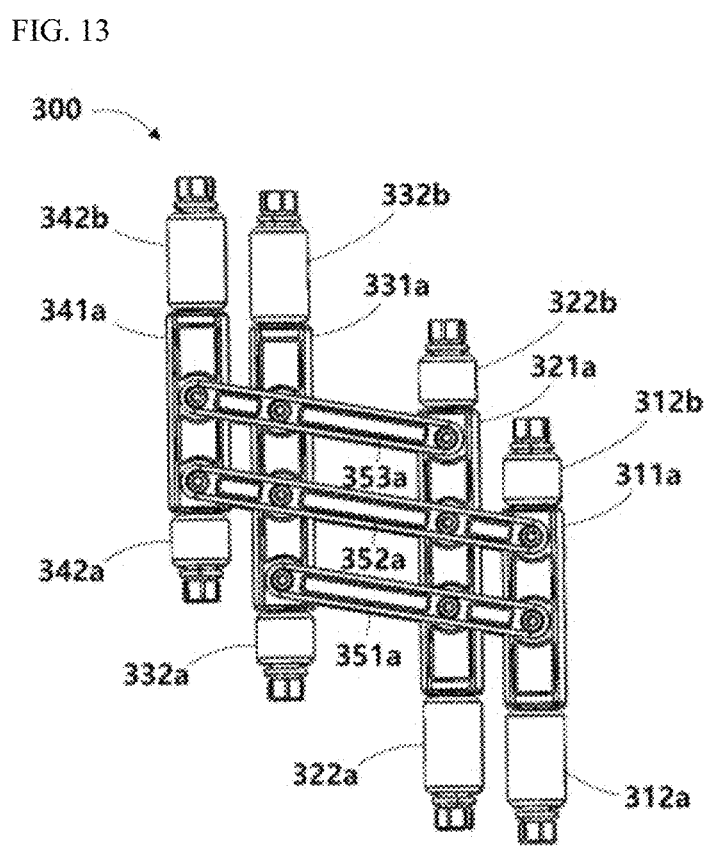
Figure 14:
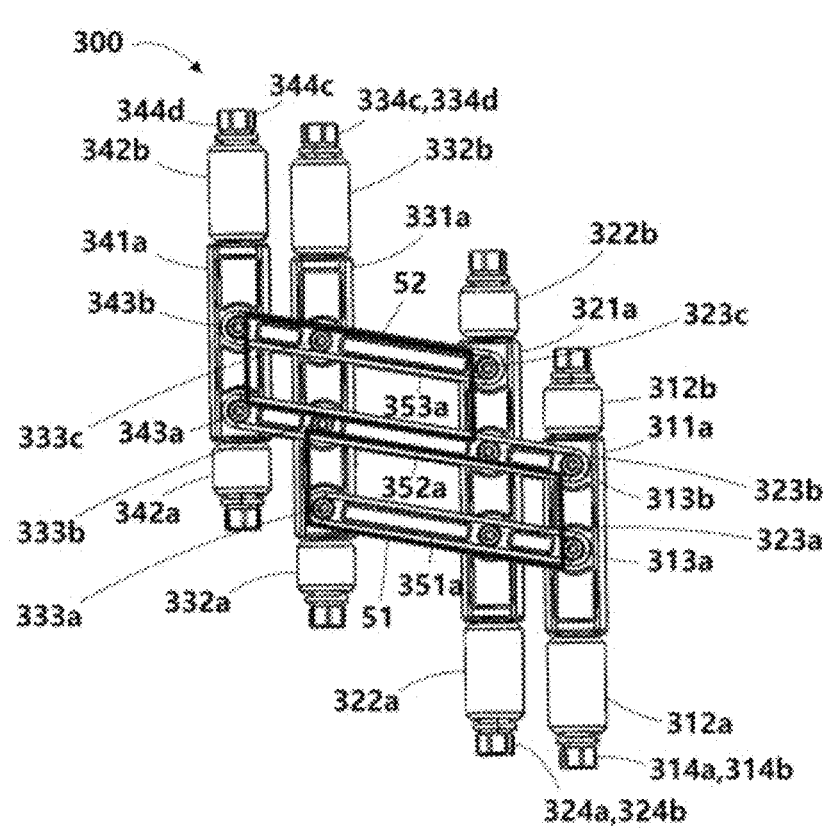
FIG. 14 is a view illustrating first and second parallelograms of the double parallelogram device for pituitary surgery according to the third embodiment of the present invention.
Figure 15:
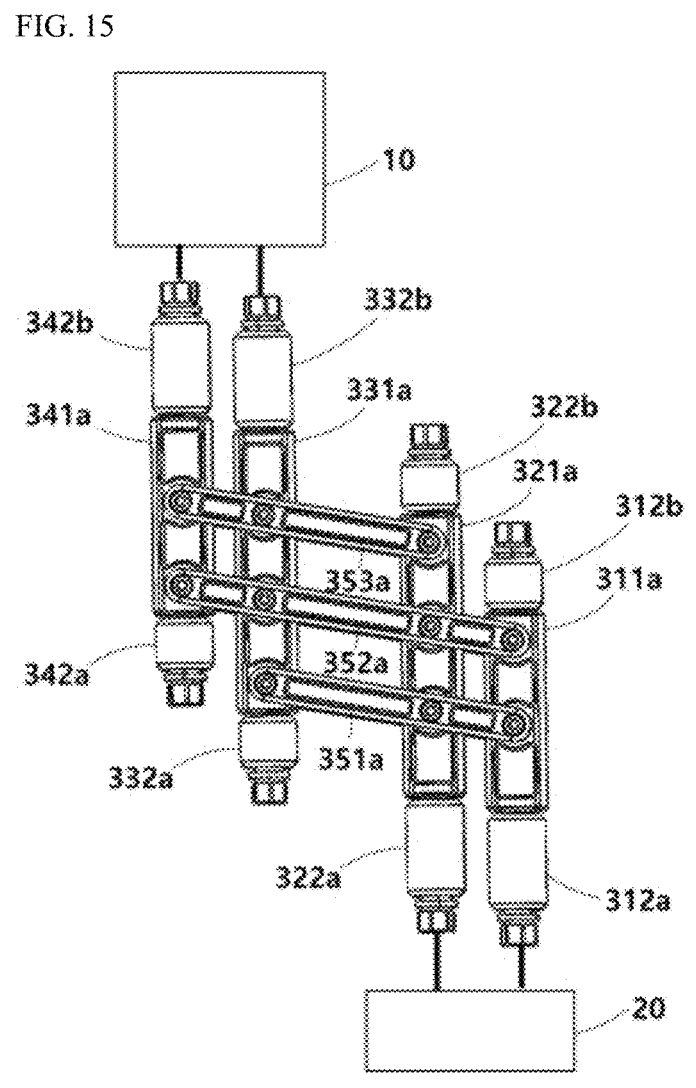

As illustrated in FIGS. 13 to 15, a double parallelogram device for pituitary surgery according to a third embodiment of the present invention forms a double parallelogram to pitch-rotate and roll-rotate according to a control driving of a driving unit 10, thereby allowing a surgical end-effector 20 to be oriented and positioned. The pituitary surgery includes, e.g., nose and brain surgery. Hereinafter, the double parallelogram device for pituitary surgery according to the third embodiment of the present invention will be described in detail with reference to accompanying FIGS. 13 to 15.

Referring to FIGS. 1 and 13, a double parallelogram unit 300 for pituitary surgery may be obtained by rotating the double parallelogram unit 100 for intraocular surgery. Thus, descriptions of a configuration and a function of each unit will be replaced by those of the first embodiment.

As illustrated in FIG. 14, a virtual first parallelogram 51 and a virtual second parallelogram 52 may be formed by connecting respective joint connection points of first and second left pitch joint units 313*a* and 313*b*, first, second, and third left pitch joint units 323*a*, 323*b*, and 323*c*, first, second, and third left pitch joint units 333*a*, 333*b*, and 333*c*, and the first and second left pitch joints 343*a* and 343*b* are connected in the horizontal and vertical directions based on FIG. 14. The first parallelogram 51 and the second parallelogram 52 are formed at upper and lower sides based on a virtual vertical line. The first parallelogram 51 is disposed lower than the second parallelogram 52

The first parallelogram 51 is formed by connecting respective joint connection points of the first and second left pitch joint units 313*a* and 313*b*, the first and second left pitch joint units 323*a* and 323*b*, and the first and second left pitch joint units 333*a* and 333*b* in a "rectangular shape" or a "square shape". The second parallelogram 52 is formed by connecting respective joint connection points of the second and third left pitch joint units 323*b* and 323*c*, the second and third left pitch joint units 333*b* and 333*c*, and the first and second left pitch joint units 343*a* and 343*b* in a "rectangular shape" or a "square shape". The first parallelogram 51 and the second parallelogram 52 share some overlapped joint units to contact each other.

As illustrated in FIGS. 11 and 12, a surgical end-effector 20 is coupled to first and second front roll link units 312*a* and 322*a* and front roll joint units 314*a*, 314*b*, 324*a*, and 324*b* disposed adjacent to the first parallelogram 51, and a driving unit 10 is coupled to first and second rear roll link units 332*b* and 342*b* and rear roll joint units 334*c*, 334*d*, 344*c*, and 344*d* disposed adjacent to the second parallelogram 52.

In describing the present invention, descriptions of related art and matters obvious to those skilled in the art can be omitted, and descriptions of these omitted components (methods) and functions will be sufficiently referred to within a range without departing from the scope and spirit of the invention. It is also understood that the above-described components of the present invention have been described for convenience of description, but components that have not been described herein can be added within a range without departing from the scope and spirit of the invention.

The component and function of each part described above have been separately described for convenience of explanation, but any one component and function may be integrated with or divided into other components as necessary.

Although the embodiments of the present invention have been described, it is understood that the present invention should not be limited to these embodiments but various changes and modifications can be made by one ordinary skilled in the art within the spirit and scope of the present invention as hereinafter claimed. Moreover, detailed descriptions related to well-known functions or configurations will be ruled out in order not to unnecessarily obscure subject matters of the present invention.

The invention claimed is:

1. A surgical double parallelogram device characterized by comprising:

a plurality of pitch and roll module units forming a plurality of stages and providing two degrees of freedom for each module to dependently pitch-rotate and roll-rotate; and a plurality of pitch link units connected to the plurality of pitch and roll module units to form a double parallelogram, wherein:

the plurality of pitch and roll module units are jointly connected to each other by the plurality of pitch link units while being spaced a predetermined distance in parallel from each other in a first direction;

the plurality of pitch link units jointly connect the plurality of pitch and roll module units in a second direction perpendicular to the first direction;

the plurality of pitch and roll module units comprise a first pitch and roll module unit, a second pitch and roll module unit, a third pitch and roll module unit, and a fourth pitch and roll module unit sequentially arranged in stages;

the first pitch and roll module unit comprises a first base link unit, the second pitch and roll module unit comprises a second base link unit, the third pitch and roll module unit comprises a third base link unit, and the fourth pitch and roll module unit comprises a fourth base link unit, each of the first, second, third, and fourth base link units being jointly connected to the plurality of pitch link units in the second direction;

each of the first, second, third, and fourth base link units comprises a left base link unit and a right base link unit;

each of the first, second, third, and fourth pitch and roll module units further comprises:

a roll link unit connected to the respective base link unit to roll-rotate;

a pitch joint unit configured to jointly connect the respective base link unit and the plurality of pitch link units so that each of the respective base link unit and the plurality of pitch link units pitch-rotates; and a roll joint unit configured to jointly connect the respective base link unit and the roll link unit so that each of the respective base link unit and the roll link unit roll-rotates;

wherein:

for each of the first and fourth base link units, the left base link unit thereof is jointly connected to the plurality of pitch link units at two points, and the right base link unit thereof is jointly connected to the plurality of pitch link units at two points; and for each of the second and third base link units, the left base link unit thereof is jointly connected to the plurality of pitch link units at three points, and the right base link unit thereof is jointly connected to the plurality of pitch link units at three points; and wherein the first and fourth base link units are disposed at respective opposite outermost positions among the first, second, third, and fourth base link units along the first direction, and the second and third base link units are disposed between the first and fourth base link units along the first direction.

2. The surgical double parallelogram device of claim 1, characterized in that the plurality of pitch link units comprise:

first, second, and third left pitch link units spaced a predetermined distance in parallel from each other so as to be jointly connected to the plurality of base link units in the second direction and at the left side; and first, second, and third right pitch link units spaced a predetermined distance in parallel from each other so as to be jointly connected in pairs to the plurality of base link units in the second direction and at the right side.

3. The surgical double parallelogram device of claim 2, characterized in that the plurality of pitch and roll module units comprise:

a first pitch and roll module unit in which each of the first and second left pitch link units and the first and second right pitch link units is jointly connected in pairs to the first base link unit;

a second pitch and roll module unit in which each of the first, second, and third left pitch link units and the first, second, and third right pitch link units is jointly connected in pairs to the second base link unit;

a third pitch and roll module unit in which each of the first, second, and third left pitch link units and the first, second, and third right pitch link units is jointly connected in pairs to the third base link unit; and a fourth pitch and roll module unit in which each of the second and third left pitch link units and the second and third right pitch link units is jointly connected in pairs to the fourth base link unit.

4. The surgical double parallelogram device of claim 3, characterized in that a surgical end-effector is connected and coupled to one roll link unit of the first and second pitch and roll module units, and a driving unit is connected and coupled to another roll link unit of the third and fourth pitch and roll module units.

5. The surgical double parallelogram device of claim 1, characterized in that each module of the plurality of stages dependently pitch-rotates and roll-rotates.

* * * * *